United States Patent [19]
Holt et al.

[11] Patent Number: 5,563,700
[45] Date of Patent: Oct. 8, 1996

[54] METHOD AND APPARATUS FOR TESTING THE MATERIAL INTEGRITY OF A CONVERTED CAN END

[75] Inventors: Steven W. Holt; Jack Fletcher; Shu An, all of Sidney, Ohio

[73] Assignee: Aluminum Company of America, Pittsburgh, Pa.

[21] Appl. No.: 437,110

[22] Filed: May 5, 1995

[51] Int. Cl.$^6$ .............................. G01N 21/00; G01N 904; B07C 5/00
[52] U.S. Cl. .................... 356/237; 356/240; 250/223 B; 250/223 R; 209/585; 209/577; 209/588
[58] Field of Search .................... 209/524, 526, 209/529, 577, 585, 587, 576; 362/297–298; 359/868–869, 851, 853; 356/239–240, 237; 250/223 B, 223 R, 559.42, 559.43, 559.45

[56] References Cited

U.S. PATENT DOCUMENTS

| | | | |
|---|---|---|---|
| 3,709,598 | 1/1973 | Vandenberg et al. | 209/585 |
| 3,745,325 | 7/1973 | Harvey | 359/869 |
| 3,826,923 | 7/1974 | Trimble et al. | 250/572 |
| 3,991,882 | 11/1976 | Fahuestock et al. | 209/588 |
| 4,086,497 | 4/1978 | Murray | 250/223 R |
| 4,095,881 | 6/1978 | Maddox | 362/298 |
| 4,351,437 | 9/1982 | Loug | 209/585 |
| 4,465,204 | 8/1984 | Kaminski et al. | 220/269 |
| 4,503,631 | 3/1985 | Kelly | 40/602 |
| 4,739,152 | 4/1988 | Downs | 362/298 |
| 4,905,263 | 2/1990 | Larsson et al. | 378/89 |
| 5,272,570 | 12/1993 | Yoshida | 359/869 |

Primary Examiner—Frank Gonzalez
Assistant Examiner—Jason D. Eisenberg
Attorney, Agent, or Firm—Thomas R. Trempus

[57] ABSTRACT

An apparatus and method for detecting the presence material irregularities and holes in thin walled opaque objects such as can ends having a generally centrally disposed integral rivet formed therein. A radiation source is focused so that a substantial portion of emitted radiation is concentrated on the portion of a can end in which the rivet is formed.

9 Claims, 4 Drawing Sheets

METHOD AND APPARATUS FOR TESTING THE MATERIAL INTEGRITY OF A CONVERTED CAN END

BACKGROUND OF THE INVENTION

1. Field of the Invention

The present invention relates to both a method and a system for detecting openings in opaque objects, particularly in converted can ends that are used in beer and beverage containers. More specifically, the present invention provides improvements to photometric end tester systems.

2. Prior Art

Many metallic cans for holding beverages or other products are provided with easy-open can ends, wherein a pull tab attached to a tear strip that is defined by a scoreline in the can end may be pulled to provide an opening in the can end for dispensing the can's contents. Generally, the pull tab is retained to the can end by means of an integral rivet. The manufacture of can ends is a highly complex, high speed operation. Examples of the methods employed in the formation of a can end can be found in U.S. Pat. Nos. 4,465,204 and 4,503,631 both to Kaminski et al, and assigned to the assignee of the instant invention. These patents are incorporated herein by reference as if fully set forth.

Generally, in the manufacture of an easy-open can end, a can end shell is first formed from a metal sheet product, preferably an aluminum sheet product. The can end shell is then conveyed to a conversion press. In the typical operation of a conversion press a can end shell is introduced between an upper tool member and a lower tool member. A press ram advances the upper tool member toward the lower tool member in order to perform any of a variety of tooling operations such as rivet forming, paneling, scoring, embossing, tab securing, and final staking. One of the most difficult and complex operations is the formation of the rivet, a multiple station operation.

It is to be appreciated that the industry is constantly striving to reduce the gauge of material from which can ends are manufactured. For example, most existing ends are dimensioned as 206, 204, or 202 diameter ends. A "206 diameter" end means that the end is 2 and 6/16 inches in diameter and a "202 diameter" end means that the end is 2 and 2/16 inches in diameter. As the can end has become smaller and smaller in diameter, so also has the gauge of the metal used to fabricate the end been reduced. The 206 diameter end was typically manufactured from metal having a thickness of between about 0.0096 and 0.0106 inches, while a 202 diameter end is typically manufactured from metal having a thickness of about 0.0088 inch.

The high speed, complex cold-working of a can end shell to produce a converted easy-open can end must be continually monitored in order to ensure that the converted can end meets specifications and does not demonstrate any "leakers". A leaker is a breach in the integrity of the can end that can be in the form of a microscopic pin hole. In order to ensure that the converted can end is consistent with required specifications and does not contain any leakers, it has become the practice to inspect each converted can end. Because the leakers are typically too small to be visible to the human eye, there has been a need for a system which can rapidly detect minute openings in solid materials without sacrificing either the speed or quality of the inspection. U.S. Pat. No. 3,826,923 which is assigned to the assignee of the instant invention discloses such an inspection system. The contents of this patent are incorporated by reference as fully set forth herein. In the operation of the end inspector, each converted can end is deposited onto a transfer belt. The belt conveys the end into a light-tight area referred to as a test station. The station contains a high intensity strobe light located below the end testing area and a photo-multiplier tube located above the end test area. The converted can end is tested by flashing the strobe light and simultaneously monitoring whether the conditioned output signal of the photo-multiplier tube exceeds a preset threshold. Thus, it can be determined if the end is considered a "leaker" and should be rejected. If the end is judged satisfactory, it continues through the machine and exits to a downstream conveyor system for eventual assembly with a can body to form the finished container.

Because of the high speed production of converted can ends in a conversion press, the desire to use thinner metal and the sophistication of the conversion process, there is a need in the industry that the end testing equipment be able to identify smaller and smaller irregularities or leakers without contributing additional cycle time to the manufacturing process.

it is therefore an object of this invention to provide a reliable method for detecting at high rates of speed defects in converted can ends.

It is another object of this invention to provide an apparatus for effectively practicing the improved method of this invention.

It is another object of this invention to facilitate the enhancement of existing inspection systems through the use of a relatively uncomplicated system for upgrading such existing systems to incorporate the improved method and apparatus of the instant invention.

It is yet another object of this invention to provide a method for increasing the signal to noise ratio of leak identifying radiation transmitted through a defective converted can end.

SUMMARY OF THE INVENTION

The invention provides a process for detecting interruptions in the material integrity of a thin wall, converted can end having a central panel, a tear panel in the central panel, and a fracture scoreline defining the tear panel. The can end also includes an operating tab and an integral rivet formed in the central panel for attaching the tab to the panel adjacent the fracture scoreline. The process includes the following steps. A first radiation emission zone is defined. A second, radiation detection zone is also defined. Means are provided for positioning the converted can end between the first and second zones. The positioning means cooperates with the converted can end to substantially eliminate any desired escape of radiation from the first zone and its inadvertent transmission to the second zone. In other words, in the absence of the presence of leakers in the can end, a known, limited, predefined amount of radiation will be present in the second, radiation detection zone. The process further includes emitting bursts of radiation at a predetermined wave length and at a predetermined intensity from the first zone. The radiation bursts are concentrated proximate the integral rivet formed in the central panel. Radiation entering the second zone by means of its transmission through a leaker in the converted can end is detected and indicates an interruption in the material integrity of the converted can end.

The apparatus of this invention is a system for detecting the presence of holes or material imperfections at least as small as 1.0 micron in diameter in thin walled aluminum can ends. The apparatus includes means for storing energy and radiation means utilizing the energy and functioning as a source of emitted bursts of radiation at a predetermined wave length and intensity. Radiation detection means are disposed so as to be responsive to the predetermined wave length. Conveyor means are provided to position the can ends between the radiation generation means and the detection means. The can ends are moved into a position between the radiation source and the detection means. The improvement to this apparatus is a means for concentrating the bursts of radiation onto a predetermined location of the thin walled aluminum can ends. Preferably, the burst of radiation is focused onto the inside of a can end rivet from the product side of the can end. The means for concentrating the bursts of radiation is a reflector means, preferably an ellipsoidal reflector that concentrates the bursts of radiation onto the aforedescribed predetermined location of the thin walled aluminum can end.

BRIEF DESCRIPTION OF THE DRAWINGS

The above as well as other features and advantages of the instant invention can be appreciated through consideration of the several drawings in which.

DESCRIPTION OF THE PREFERRED EMBODIMENT

Figure 1A:
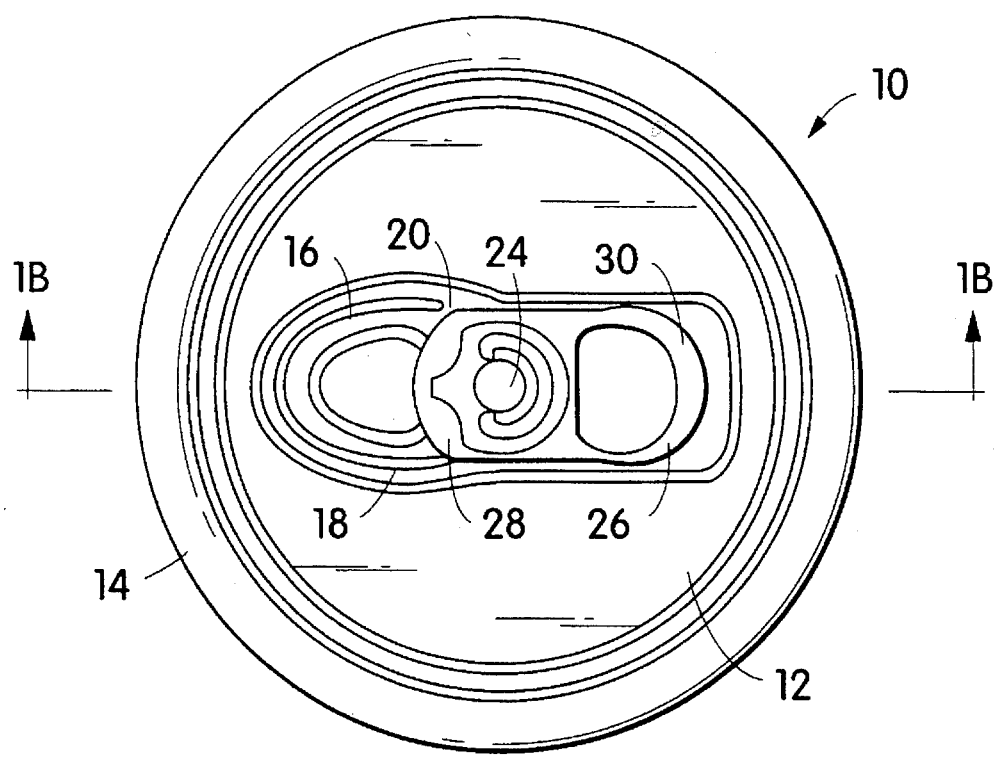
FIG. 1A is a top plan view of an easy-open can end.
Figure 1B:
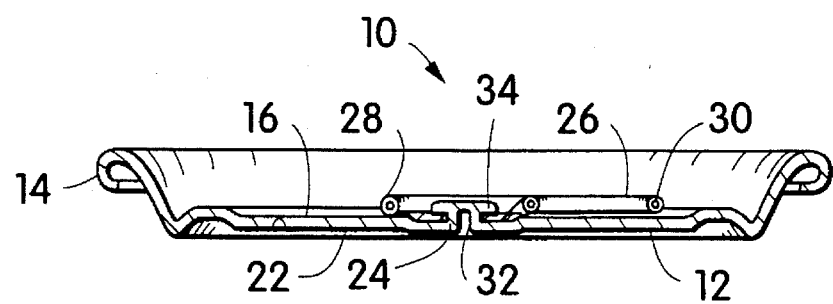
FIG. 1B is a cross sectional side view along lines 1B—1B of FIG. 1A.

In order to appreciate the improvements and benefits that the instant invention provides to end inspection equipment, it is first necessary to review the configuration of a typical beer and beverage can end. A stay-on-tab easy open can end is designated by reference character 10 in FIGS. 1A and 1B. Can end 10 has an end panel 12 of generally circular shape which includes a circumferentially extending raised edge 14 for attaching the can end 10 to a suitable cylindrical beverage can (not shown) or the like. In general, the can end 10 will be manufactured of a relatively ductile metal such as, for example, aluminum, but it may be made from other acceptable materials as required. A retained tear strip 16 extends across can end 10 from a position spaced inwardly of raised edge 14 to approximately the center of can end 10. Tear strip 16 is defined by a generally U-shaped score line 18 with open end 20 of the U positioned toward the center of can end 10. A score line 18 is interrupted so that tear strip 16 will be captively retained on the underside or product side, 22 of can end 10 when torn open.

An integral rivet 24 is positioned adjacent open end 20 of U-shaped score line 18, and a graspable ring-like pull tab 26 which may be of any desired size and configuration is secured to can end 10 by means of rivet 24. Pull tab 26 is provided with a nose portion 28 to initiate the tear along score line 18 upon lifting of pull tab 26 whereupon tear strip 16 is torn open as is well known in the art. As can be seen, pull tab 26 is provided with a finger portion 30 opposite the nose portion 28. It is to be appreciated that the industry is constantly striving to reduce the gauge of material from which can ends are manufactured. The rivet 24 includes a generally cylindrical portion 32 that is vertically disposed relative to the end panel 12. During the conversion process the rivet is formed during multiple cold working steps that form and reform a portion of the panel first into a bubble and finally a rivet adapted to receive the pull tab thereon. Methods of rivet development utilizing the prior art can be found in U.S. Pat. Nos. 4,465,204 and 4,530,631 to Kaminski et al, assigned to the assignee of the instant invention and incorporated herein by reference. The top portion 34 of the rivet is flattened to have a diameter slightly greater than the cylindrical portion 32. The flattened portion 34 is created as the individual pull tab 26 is staked to the rivet 24 during the conversion process. As a result the rivet consists of metal that is of a reduced gauge relative to the remainder of the can end due to the extensive cold working of the metal. Additionally, because of the extensive cold working, the rivet is the specific component of, and represents the particular location on, the can end that is most likely to experience a "leaker."

Figure 2:
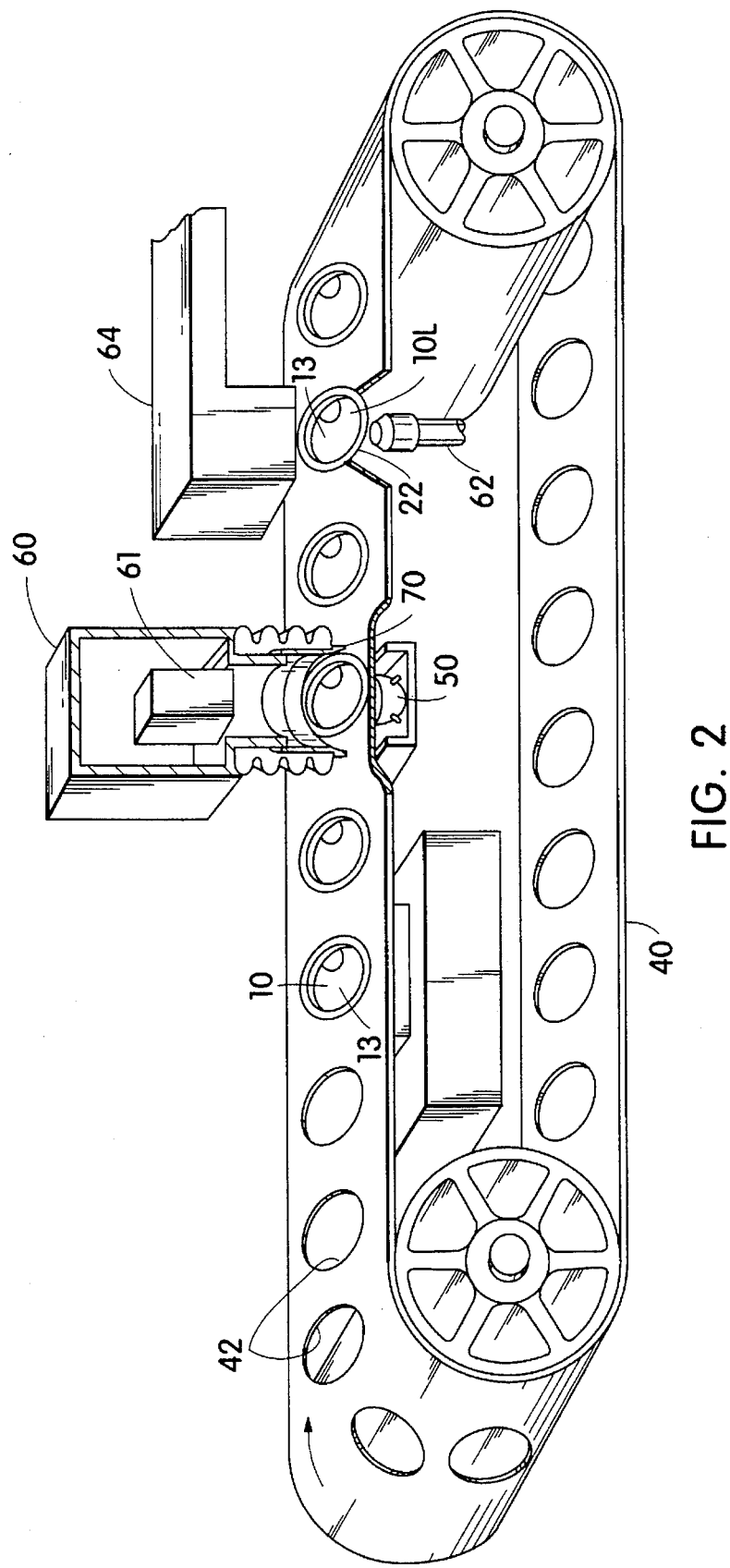
FIG. 2 is a side elevation view of a system for detecting openings in an opaque object.

Turning now to FIG. 2, a mechanism generally employing the system of the invention is illustrated. In this embodiment, a converted easy-open can end 10 having a public side 13 and a product side 22 is carried on an endless belt 40 to a detection station wherein the easy-open end 10 is exposed to a very short pulse of high intensity radiation from a source 50. Radiation source 50, which will be described in detail below in conjunction with FIG. 3, includes a gas-filled ionizable source, such as, for example a xenon gas-filled source. Belt 40 is formed with openings as at 42 which support the ends 10 and permit any radiation which passes through an opening in the converted can end 10 to pass through the belt into a radiation detector 60. A vacuum means 70 located beneath the belt and around the radiation source 50 can be used to provide a light-tight seal between the belt 40 and the lip 14 of the can end 10.

During the pulse from the high intensity radiation source, some radiation passes through any openings or material irregularities in the converted can end (as well as through the opening 42 in the belt 40). The radiation having so passed is detected by a means for detecting radiation 61 such as, for example, a solid state device, or as preferably employed, a photomultiplier tube (PMT). The radiation detecting means generates an electrical output signal by means well known to those skilled in the art. If the PMT's output signal exceeds a preset threshold, the end is considered a leaker and is subsequently rejected. A rejection means typically comprises a pneumatic source 62 that urges the "leaker" end 10L from the belt 40 into a rejected end collection means 64. The rejected end is then conveyed to a scrap collection and recycle means, not shown. If the end is not a leaker, it continues through the machine and exits to downstream conveying equipment that is know in the industry and not illustrated herein. The radiation detector is particularly intended for use in an automated system wherein each converted can end will only be analyzed for a very short period of time. For example, in the system shown, it is contemplated that as many as 600 or more can ends can be analyzed in one minute, a rate of approximately ten or more ends per second. Each can end thus must be moved into position, irradiated, and moved off the detecting station in a period of approximately one-tenth of a second. Theoretically, the can end can only be irradiated for up to one-tenth of a second and, of course, practically for only a much shorter period of time probably only about 100 microseconds, or less since the can end as it is moved by the belt is only correctly aligned between the radiation source 50 and the detector 60 for a short period of time.

Figure 3:
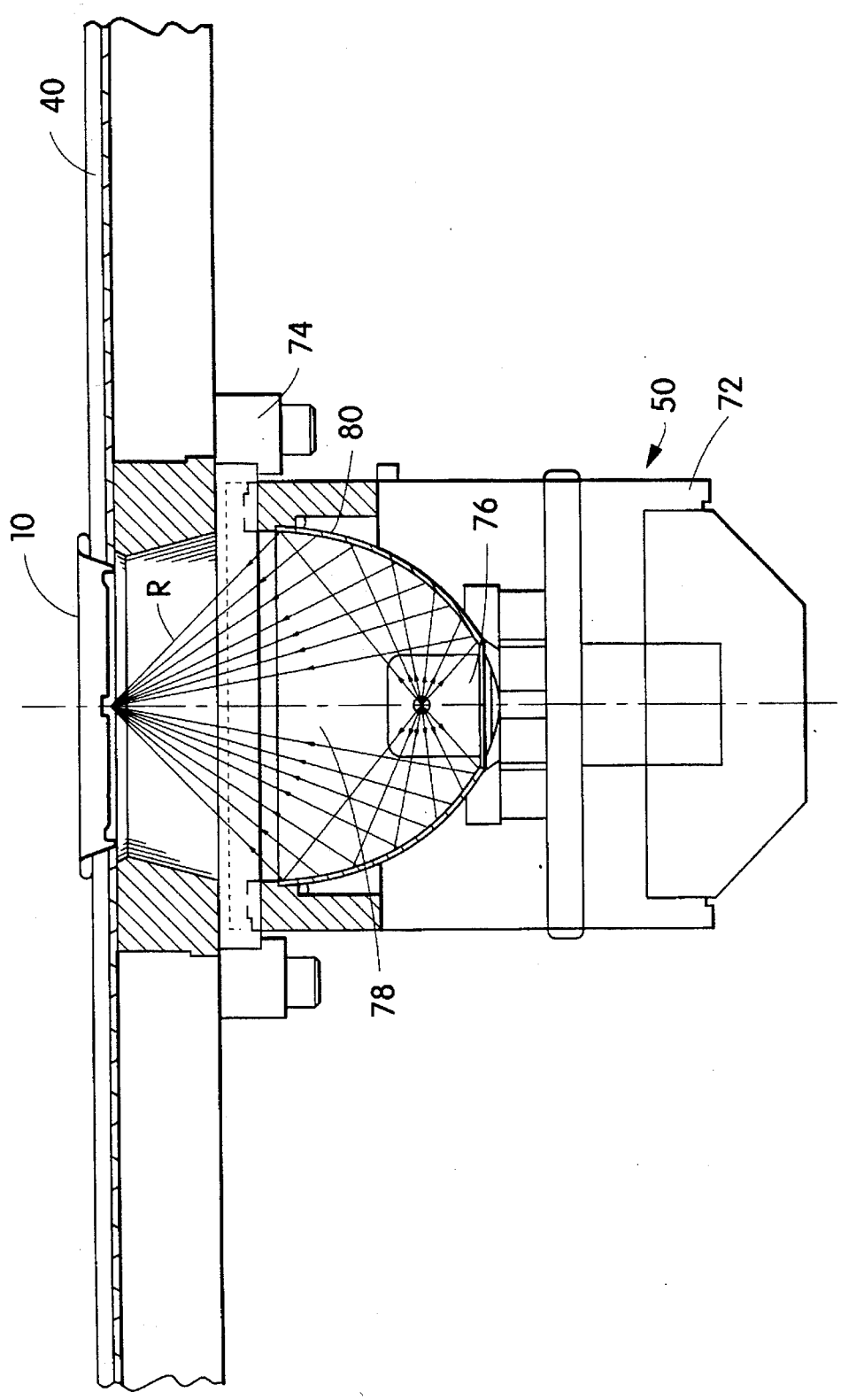
FIG. 3 is a side elevation cross sectional view of an improved device for concentrating bursts of radiation onto a predetermined location of a thin walled aluminum can end.

Turning now to FIG. 3, an improved radiation source and radiation concentrating means is shown in cross section. The radiation source 50 includes a housing 72 and is supported below the moveable belt 40 by means of a support structure 74. The radiation source is preferably a xenon tube 76 centrally disposed within the support housing 72. An example of the circuitry by which the radiation source is triggered is set forth in U.S. Pat. No. 3,826,923. The radiation source 76 is mounted within a test chamber 78 that is defined in part by an upper boundary consisting of the converted can end 10 supported by the belt 40 and a combined lower and side wall boundary defined by a reflector 80. Reflector 80 is preferably an ellipsoidal reflector that concentrates or focuses the radiation on the rivet area on the converted can end. In the preferred embodiment of this invention, the reflector 80 is electroformed nickel with a rhodium coating. An ellipsoidal reflector suitable for use according to the teachings of this invention is available commercially from Sky Tracker, Inc.

Figure 4:
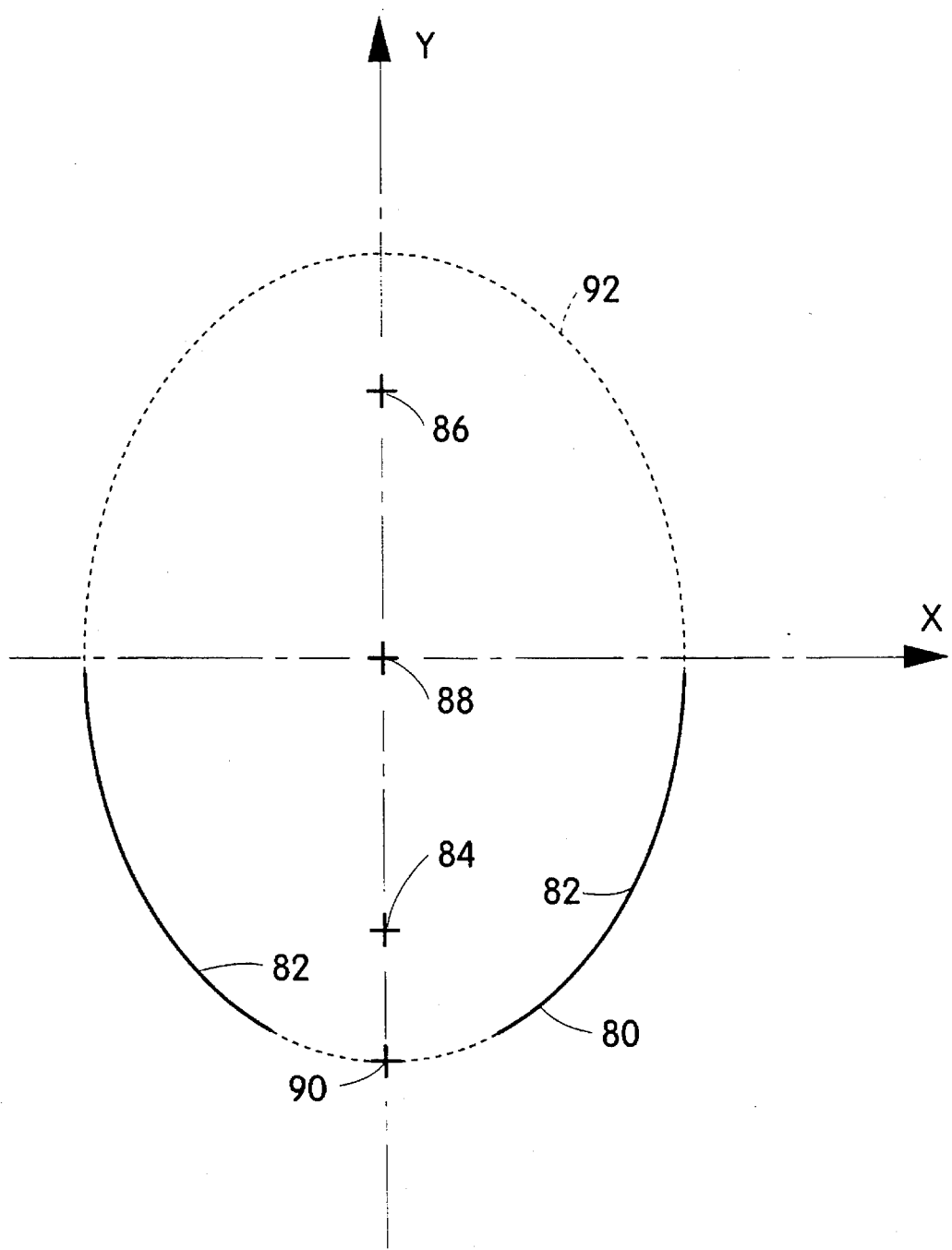
FIG. 4 is a diagrammatic representation of the ellipsoidal radiation concentration device.

Turning also to FIG. 4, a schematic representation of the ellipsoidal reflector 80 illustrates the useful reflector surface indicated in solid line and by the reference character 82. A primary focal point 84 corresponds with the location of the radiation source, or Xenon tube 76. A secondary focal point 86 corresponds with the placement of the can end rivet during can end testing. Generally, the primary focal point 84 and secondary focal point 86 are equally distanced from the intersection or origin 88 of the x and y axes of the ellipsoidal reflector 80. The vertex 90 of the ellipsoidal reflector surface is shown in dotted line, as is the upper portion 92 of the ellipsoidal shape. In operation, the belt 40 conveys the can end 10 through a plane that is parallel to the x axis of the ellipsoidal reflector 80. The radiation originating at the primary focal point 84 is concentrated at the secondary focal point 86.

FIG. 3 also illustrates the reflected light or ray path as at "R" that is obtained through the use of the above described configuration. According to the instant invention, the preferred point of focus for the emitted radiation is the location of the rivet in the center of the can. As described above, a substantial portion of the converted can end is relatively planer and as a result, leakers are generally readily susceptible to detection. However, because of the complexity of the configuration of the rivet, it is critical that sufficient radiation penetrate the area defined by the product side of the rivet. It has been found that the light or radiation energy in the rivet area resulting from the instant invention is more than four times the amount that had been available in existing designs. Likewise, the output of the photo-multiplier tube signal in the detector positioned above the converted can end was found to be approximately two to three times that of prior designs. These improvements are accomplished with no change to the light source or detectors. The duration of radiation emission used on an end tester as shown herein is typically a few microseconds or less at a predetermined wavelength of between about 300 to 1000 nanometers. The response of a PMT is about 100 nanoseconds or less. It has been found that the concentration of radiant energy on a focal point such as the rivet of a converted can end improves the capability of an end tester to detect leakers in a can end. By way of example, it has been found that with the use of the improved reflector, radiation passing through a one micron hole in the rivet area, or center portion of the can end, is sufficient to provide a detector signal output increase of 3.2 times that of the prior design. By the use of the new design, it has been demonstrated that approximately 63% of the available radiant energy is focused at or near the center or rivet area of the converted can end. Thus, the area of the can end most susceptible to damage during the conversion process can be more thoroughly inspected and minute irregularities in the integrity of the material detected.

What has been described is an improved method and apparatus for the inspection of opaque objects such as converted can ends.

What is claimed is:

1. In an apparatus for detecting the existence of interruptions in the material integrity of thin walled can ends having a generally centrally disposed integral rivet formed therein, said apparatus having (a) means for storing energy, (b) radiation means utilizing said energy and comprising a gas filled ionizable source emitting bursts of radiation at a predetermined wavelength and intensity, (c) radiation detection means responsive to the predetermined wavelength, and (d) means for positioning said can ends between said radiation generating means and said detection means; the improvement comprising: ellipsoidal reflector means for concentrating the bursts of radiation onto the integral rivet of said thin walled can ends.

2. A process for detecting interruptions in the material integrity of a thin walled, converted can end having a central panel and a tear panel in said central panel, said tear panel defined by a fracture score line surrounding a portion of the periphery of said tear panel, an operating tab, and an integral rivet formed in said central panel and attaching said tab to said end adjacent said fracture score line, said process consisting of the steps of:

defining a first radiation emission zone and a second radiation detection zone;

providing positioning means for disposing said converted can end between said first and second zones, said positioning means cooperating with said converted can end to substantially eliminate any undesired escape of radiation from said first zone to said second zone;

emitting bursts of radiation at a predetermined wave length and intensity from said first zone;

concentrating said bursts of radiation proximate the integral rivet formed in said central panel;

detecting any radiation entering into said second zone through any interruptions in the material integrity of said converted can end.

3. The process according to claim 2 wherein the predetermined wave length is between about 300 and 1000 nanometers.

4. A method for improving the signal to noise ratio in an apparatus for testing the material integrity of a converted can end, said apparatus having (a) means for storing energy, (b) radiation generating means utilizing said energy and comprising a gas filled ionizable source emitting bursts of radiation at a predetermined wavelength and intensity, (c) radiation detection means responsive to the predetermined wavelength, and (d) means for positioning said can ends between said radiation generating means and said detection means; said method comprising the step of concentrating the bursts of radiation onto a predetermined location of said converted can end.

5. The method for improving the signal to noise ratio in an apparatus for testing the material integrity of a converted can end according to claim 4 wherein the can end has a generally centrally disposed integral rivet formed therein, and wherein the predetermined location of said converted can end is said centrally disposed rivet.

6. The method for improving the signal to noise ratio in an apparatus according to claim 4 wherein the step of concentrating the radiation onto a predetermined location is effected by the use of a reflector means disposed about the radiation generating means.

7. A process for detecting interruptions in the material integrity of a thin walled, opaque object having a definable central portion, said process defining a first radiation emission zone and a second radiation detection zone;

providing positioning means for disposing said opaque object between said first and second zones, said positioning means cooperating with said opaque object to substantially eliminate any undesired escape of radiation from said first zone to said second zone;

emitting bursts of radiation at a predetermined wave length and intensity from said first zone;

concentrating said bursts of radiation at the definable central portion of said opaque object;

detecting any radiation entering into said second zone through any interruptions in the material integrity of said opaque object.

8. The process according to claim 7 wherein the step of concentrating the bursts of radiation is effected by the use of a reflector means disposed about a source of radiation.

9. The process according to claim 8 wherein the reflector means is an ellipsoidal reflector.

* * * * *